United States Patent [19]
Alvarez

[11] Patent Number: 5,830,667
[45] Date of Patent: Nov. 3, 1998

[54] HUMAN P450 IID6 CYTOCHROME-DERIVED PEPTIDE FRAGMENTS, ANTI-PEPTIDE FRAGMENT ANTIBODIES, APPLICATIONS THEREOF IN THE DIAGNOSIS OF AUTOIMMUNE HEPATITIS

[75] Inventor: Fernando Alvarez, Meudon, France

[73] Assignee: Institut National de la Sante et de la Recherche Medicale-INSERM, Paris Cedex, France

[21] Appl. No.: 162,149
[22] PCT Filed: Jun. 16, 1992
[86] PCT No.: PCT/FR92/00539
  § 371 Date: Apr. 18, 1994
  § 102(e) Date: Apr. 18, 1994
[87] PCT Pub. No.: WO92/22656
  PCT Pub. Date: Dec. 23, 1992

[30] Foreign Application Priority Data

Jun. 17, 1991 [FR] France ................................. 91 07363

[51] Int. Cl.$^6$ ....................... G01N 33/53; G01N 33/564; C07N 14/435; C07N 16/18
[52] U.S. Cl. ....................... 435/7.1; 435/7.2; 435/975; 435/7.72; 435/7.92; 435/7.93; 435/7.94; 435/7.95; 435/331; 435/332; 436/506; 436/536; 436/811; 436/820; 530/300; 530/324; 530/325; 530/326; 530/327; 530/328; 530/401; 530/387.9; 530/388.2; 530/389.1; 530/868; 530/391.1
[58] Field of Search ............................ 424/172.1, 185.1; 435/7.1, 70.21, 172.2, 240.27, 7.2, 7.92, 7.93, 7.94, 7.95; 514/2; 530/324, 325, 326, 327, 328, 329, 330, 331, 401, 388.27, 389.2, 391.1, 300, 350, 387.9, 388.85, 868, 391.3, 389.1; 436/506

[56] References Cited

U.S. PATENT DOCUMENTS 5,106,726  4/1992  Wang .......................................... 435/5

OTHER PUBLICATIONS

Hurtenbach et al., J. Exp. Med., 177:1499–1504, 1993.
Gonzalez et al., Nature, 331: 442–446, 1988.
Yamamoto et al., Eur. J. Immunol, 23: 1105–1111, 1993.
Godins, Chapter 3, from: "Monoclonal Antibodies: Principles and Practices", pp. 59–103, Academic Press, 1986.
Waldmann, Science, 252:1657–62, 1991.
Harris et al., TIBTECH, 11: 42–44, 1993.
Edginston, Bio/Technology, 10: 383–389, 1992.
Proceedings of the National Academy of Sciences of USA. vol. 85, Nov. 1988, Washington US, pp. 8256–8260; U.R. Zanger et al.: "Antibodies against human cytochrome P450dbl in autoimmune hepatitis type II".
Biochemical and Biophysical Research Communications, vol. 159, No. 2, Mar. 15, 1989, Duluth, Minnesota, US; pp. 542–547; M. Gueguen et al; "Anti–Liver kidney microsome antibody type I recognizes human cytochrome P450dbl".
The Journal of Clinical Investigation, vol. 88, No. 4, Oct. 1991, New York, pp. 1370–1378; M.P. Manns et al: "LKM–1 Autoantibodies recognize a short linear sequence in P450IID6, a cytochrome P–450 Monoxygenase".

Primary Examiner—Ronald B. Schwadron
Attorney, Agent, or Firm—Oblon, Spivak, McClelland, Maier & Neustadt, P.C.

[57] ABSTRACT

Human P450 IID6 cytochrome-derived peptide fragments, anti peptide anti fragment antibodies and applications thereof in the diagnosis of autoimmune hepatitis and more especially in the differential diagnosis between autoimmune hepatitis and other chronic viral forms of hepatitis, such as hepatitis C or B. Said human P450 cytochrome peptide fragment contains at least one P450 IID6 cytochrome immunodominant epitope and consists of an amino acid sequence comprising from 3 to 70 amino acids. Said peptide binds specifically with anti-LKM auto-anitbodies produced in autoimmune hepatitis.

5 Claims, 3 Drawing Sheets

SEQUENCE LISTING ( 1 ) GENERAL INFORMATION:

( i i i ) NUMBER OF SEQUENCES: 10

( 2 ) INFORMATION FOR SEQ ID NO:1:

( i ) SEQUENCE CHARACTERISTICS:
        ( A ) LENGTH: 39 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:1:

```
Lys Val Leu Arg Phe Gln Lys Ala Phe Leu Thr Gln Leu Asp Glu Leu
1               5                   10                  15

Leu Thr Glu His Arg Met Thr Trp Asp Pro Ala Gln Pro Pro Arg Asp
            20                  25                  30

Leu Thr Glu Ala Phe Leu Ala
            35
```

( 2 ) INFORMATION FOR SEQ ID NO:2:

( i ) SEQUENCE CHARACTERISTICS:
        ( A ) LENGTH: 18 amino acids (B) TYPE: amino acid
(C) STRANDEDNESS: single
(D) TOPOLOGY: linear (ii) MOLECULE TYPE: peptide (xi) SEQUENCE DESCRIPTION: SEQ ID NO:2:

```
Leu Leu Thr Glu His Arg Met Thr Trp Asp Pro Ala Gln Pro Pro Arg
1               5                   10                  15

Asp Leu
```

(2) INFORMATION FOR SEQ ID NO:3:

(i) SEQUENCE CHARACTERISTICS:
        (A) LENGTH: 13 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:3:

```
Glu His Arg Met Thr Trp Asp Pro Ala Gln Pro Pro Arg
1               5                   10
```

(2) INFORMATION FOR SEQ ID NO:4:

(i) SEQUENCE CHARACTERISTICS:
        (A) LENGTH: 70 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:4:

```
Ala Lys Gly Asn Pro Glu Ser Ser Phe Asn Asp Glu Asn Leu Arg Ile
1               5                   10                  15

Val Val Ala Asp Leu Phe Ser Ala Gly Met Val Thr Thr Ser Thr Thr
                20                  25                  30

Leu Ala Trp Gly Leu Leu Leu Met Ile Leu His Pro Asp Val Gln Arg
                35                  40                  45

Arg Val Gln Gln Glu Ile Asp Asp Val Ile Gly Gln Val Arg Arg Pro
            50                  55                  60

Glu Met Gly Asp Gln Ala
65                  70
```

(2) INFORMATION FOR SEQ ID NO:5:

(i) SEQUENCE CHARACTERISTICS:
        (A) LENGTH: 13 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:5:

```
Ala Lys Gly Asn Pro Glu Ser Ser Phe Asn Asp Glu Asn
1               5                   10
```

(2) INFORMATION FOR SEQ ID NO:6:

(i) SEQUENCE CHARACTERISTICS:
        (A) LENGTH: 43 amino acids
        (B) TYPE: amino acid
        (C) STRANDEDNESS: single (D) TOPOLOGY: linear (ii) MOLECULE TYPE: peptide (xi) SEQUENCE DESCRIPTION: SEQ ID NO:6:

Met Val Thr Thr Ser Thr Thr Leu Ala Trp Gly Leu Leu Leu Met Ile
1               5                   10                  15

Leu His Pro Asp Val Gln Arg Arg Val Gln Gln Glu Ile Asp Asp Val
                20                  25                  30

Ile Gly Gln Val Arg Arg Pro Glu Met Gly Asp
                35                  40

(2) INFORMATION FOR SEQ ID NO:7:

(i) SEQUENCE CHARACTERISTICS:
                (A) LENGTH: 31 amino acids
                (B) TYPE: amino acid
                (C) STRANDEDNESS: single
                (D) TOPOLOGY: linear (ii) MOLECULE TYPE: peptide (xi) SEQUENCE DESCRIPTION: SEQ ID NO:7:

Met Ile Leu His Pro Asp Val Gln Arg Arg Val Gln Gln Glu Ile Asp
1               5                   10                  15

Asp Val Ile Gly Gln Val Arg Arg Pro Glu Met Gly Asp Gln Ala
                20                  25                  30

(2) INFORMATION FOR SEQ ID NO:8:

(i) SEQUENCE CHARACTERISTICS:
                (A) LENGTH: 41 amino acids
                (B) TYPE: amino acid
                (C) STRANDEDNESS: single
                (D) TOPOLOGY: linear (ii) MOLECULE TYPE: peptide (xi) SEQUENCE DESCRIPTION: SEQ ID NO:8:

Asp Gln Ala His Met Pro Tyr Thr Thr Ala Val Ile His Glu Val Gln
1               5                   10                  15

Arg Phe Gly Asp Ile Val Pro Leu Gly Met Thr His Met Thr Ser Arg
                20                  25                  30

Asp Ile Gly Val Gln Gly Phe Arg Ile
                35                  40

(2) INFORMATION FOR SEQ ID NO:9:

(i) SEQUENCE CHARACTERISTICS:
                (A) LENGTH: 17 amino acids
                (B) TYPE: amino acid
                (C) STRANDEDNESS: single
                (D) TOPOLOGY: linear (ii) MOLECULE TYPE: peptide (xi) SEQUENCE DESCRIPTION: SEQ ID NO:9:

Gly Met Thr His Met Thr Ser Arg Asp Ile Gly Val Gln Gly Phe Arg
1               5                   10                  15

Ile (2) INFORMATION FOR SEQ ID NO:10:

(i) SEQUENCE CHARACTERISTICS:
                (A) LENGTH: 20 amino acids
                (B) TYPE: amino acid ( C ) STRANDEDNESS: single
( D ) TOPOLOGY: linear ( i i ) MOLECULE TYPE: peptide ( x i ) SEQUENCE DESCRIPTION: SEQ ID NO:10:

```
Glu Lys Pro Tyr Pro Glu His Phe Leu Asp Ala Gln Gly His Phe Val
1               5                   10                  15
Lys Pro Glu Ala
            20
```

HUMAN P450 IID6 CYTOCHROME-DERIVED PEPTIDE FRAGMENTS, ANTI-PEPTIDE FRAGMENT ANTIBODIES, APPLICATIONS THEREOF IN THE DIAGNOSIS OF AUTOIMMUNE HEPATITIS

This application is a 371 of PCT/FR92/00639, filed Jun. 16, 1992.

BACKGROUND OF THE INVENTION

The present invention relates to peptide fragments derived from human cytochrome P450 IID6 (formerly called cytochrome P450 dbl), to anti-peptide fragment antibodies and to their applications in the diagnosis of autoimmune hepatitis and more particularly in the differential diagnosis between autoimmune hepatitis and other chronic hepatitides of viral origin, such as hepatitis C or hepatitis B.

DESCRIPTION OF THE BACKGROUND

Autoimmune hepatitis, in particular in children, is an inflammatory disease which progresses into cirrhosis and hepatic insufficiency, which generally responds to an immunosuppressive treatment and is characterized by the presence of high non-organ-specific autoantibody titres.

Two subgroups have been defined, as a function of the autoantibody present in the serum: anti-smooth muscle antibody (anti-SMA) and anti-liver-kidney-microsome antibodies (anti-LKM), called hereinafter anti-LKM antibodies.

The antigen recognized by the anti-LKM antibodies is a protein with a molecular weight of 50 kDa, which is present at a relatively high concentration in the endoplasmic reticulum. Several studies suggest that this antigen corresponds to a protein of the cytochrome P450 family (WAXMAN B. J. et al., Gastroentérol. 1988, 95, 1326). This was confirmed by screening a rat liver cDNA library in the presence of an anti-50 kDa protein antibody, purified by affinity from an LKM-positive serum. Both constitutive forms of cytochrome P450, belonging to the subfamily IID 1 and 2 (rat db1 and db2), have been identified, as the antigens recognized by the anti-LKM antibody (GUEGUEN M. et al., J. Exp. Med., 1988, 168, 801).

Other studies (GUEGUEN M. et al., Biochem. Biophys. Res. Commun., 1989, 159, 542; ZANGER U. M. et al., Proc. Natl. Acad. USA, 1988, 27, 8256; MANNS M. P. et al., J. Clin. Invest., 1989, 83, 1066) have shown that cytochrome P450 IID6 is a protein recognized, in human liver, by the anti-LKM antibody.

Several methods for assaying anti-LKM antibodies have been proposed:

a first method of detection of these antibodies has been described in RIZZETTO et al., 1973, Clin. Exp. Immunol., 15, 331, and has especially been used for the diagnosis of liver diseases associated with the production of anti-LKM antibodies in children (MAGGIORE et al., J. Pediatrics, 1986, 108, 3, 399–404: *Liver-disease associated with anti-liver-kidney microsome antibody in children*); this method consists in detecting the said antibodies (serum) by indirect immunofluorescence on rat liver and kidney sections.

The sera are considered as positive for the anti-LKM antibodies when they react at a minimal dilution of 1:100 with the cytoplasm of hepatocytes and proximal renal tubules, whereas no coloration is obtained in the distal tubules.

However, this indirect immunofluorescence method has the major disadvantage of not being very sensitive and of thereby causing false negatives which can direct the clinician towards a wrong diagnosis and thereby disorient him with respect to the clinical signs observed.

Furthermore, the interpretation of the results obtained is generally difficult and is limited to specialist laboratories.

Other tests have therefore been proposed; there may be mentioned especially:

an RIA test (Clin. Exp. Immunol., 1984, 57, 600–608: *Detection of liver-kidney microsomal auto-antibodies by radioimmunoassay and their relation to anti-mitochondrial antibodies in inflammatory liver diseases*), which has the general disadvantages of RIA tests (especially difficulty of obtaining and handling labelled reagents);

ELISA tests;

in J. Ped. Gastoenterol. Nutr. 1988, 7, 816–822 (Detection of anti-endoplasmic reticulum antibody-positive autoimmune hepatitis in children, using an ELISA technique), the Authors (K. PARADIS, A. DIB, JC. HOMBERG, O. BERNARD, D. ALAGILLE and F. ALVAREZ) have described an ELISA method of detection using, as antigen, a preparation of rat liver microsomes.

This technique proved more sensitive than indirect imimunofluorescence; nevertheless it has the disadvantage of causing contamination of the antigen used by other fractions, including mitochondria, which may cause false positives, in particular in adults having, especially in primitive biliary cirrhosis, anti-mitochondrial antibodies.

Pursuing their work, the Authors (M. GUEGUEN, AM YAMAMOTO, O. BERNARD and F. ALVAREZ) replaced the liver microsomes with a fusion protein comprising cytochrome P450 (Biochem. Biophys. Res. Comm., 1989, 159, 2, 542–547).

However, such an antigen has the disadvantage of also bringing about false positives, especially because of the presence of the associated protein.

SUMMARY OF THE INVENTION

With the aim of solving the problem of obtaining a reliable and sensitive test both in children and adults (absence of false positives in all cases), the Inventor, co-Author of the abovementioned articles, has developed an autoimmune hepatitis-specific detection test which permits especially differential diagnosis with hepatitides of viral origin (especially hepatitis C). Indeed, it appeared that the hepatitis C detection test gives false positive results in subjects having in fact autoimmune hepatitis.

This is indeed very important since the treatments of viral hepatitides such as hepatitis B and C and of autoimmune hepatitis are completely different: in hepatitis B and C, recombinant interferon, which permits an improvement in the serum aminotransferase activity, is generally administered whereas in autoimmune hepatitis, it is prednisone and azathioprine which cause an improvement in this hepatitis.

It is therefore important, insofar as the prognosis and treatment of these two types of hepatitides are radically different, to be able to have available a test and reagents for autoimmune hepatitis, which have especially highly specific diagnostic properties, which can be used rapidly and which can be performed in any local medical analysis laboratory.

The present invention therefore set itself the objective of providing human cytochrome P450-derived peptide fragments which are more suitable for the requirements of practical use than the reagents of the prior art, especially in permitting the development of highly specific diagnostic tests as well as the preparation of antibodies (polyclonal and/or monoclonal) intended for therapeutic and/or diagnostic use, which are also highly specific towards at least one immunodominant epitope of autoimmune hepatitis.

The subject of the present invention is a human cytochrome P450 peptide fragment, characterized in that it contains at least one immunodominant epitope of cytochrome P450 IID6, in that it consists of an amino acid sequence which comprises between 3 and 70 amino acids and in that it binds specifically with the anti-LKM autoantibodies produced during autoimmune hepatitis.

DESCRIPTION OF THE PREFERRED EMBODIMENTS

Figure 1:
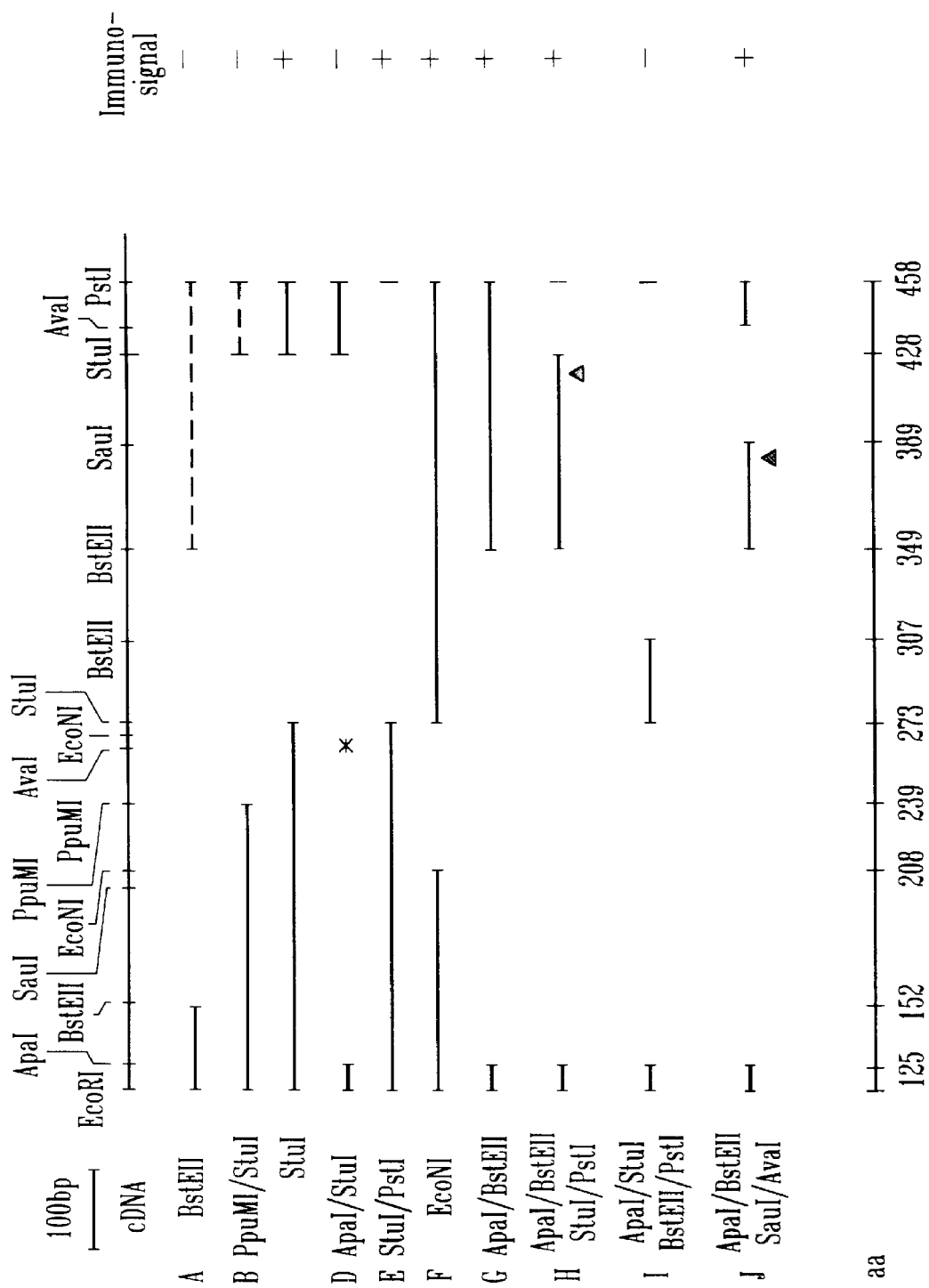
FIG. 1 is a restriction map of cytochrome P450 IID6.

For the purposes of the present invention, "peptide fragment" encompasses not only the sequences comprising a human cytochrome P450 IID6 fragment, but also those which differ from it only by substitution, deletion and addition of a small number of amino acids, on condition that the sequences thus modified have a specificity of binding with the anti-LKM autoantibodies which is equivalent to that of the abovementioned fragments.

Among these peptide fragments, there may be mentioned in particular:

a—a first set of fragments comprising at least one fragment of the sequence of cytochrome P450 IID6 between amino acid 239 and amino acid 278, and comprising the major antigenic site of cytochrome P450 and especially:

a peptide fragment, characterized in that it consists of 39 amino acids, whose sequence is of the following formula I(SEQ. ID. NO. 1):

Lys — Val — Leu — Arg — Phe — Gln — Lys — Ala — Phe — Leu — Thr — (I)
Gln — Leu — Asp — Glu — Leu — Leu — Thr — Glu — His — Arg — Met
Thr — Trp — Asp — Pro — Ala — Gln — Pro — Pro — Arg — Asp — Leu —
Thr — Glu — Ala — Phe — leu — Ala, which sequence corresponds to amino acids 239–278 of human cytochrome P450 IID6, a peptide fragment, characterized in that it consists of 18 amino acids, whose sequence is of the following formula II (SEQ ID NO. 2):

Leu-Leu-Thr-Glu-His-Arg-Met-Thr-Trp-Asp-Pro-Ala-Gln-Pro-Pro-Arg-Asp-Leu (II), which sequence corresponds to amino acids 254–271 of human cytochrome P450 IID6, a peptide fragment, characterized in that it consists of 13 amino acids whose sequence is of the following formula III (SEQ ID NO. 3):

Glu-His-Arg-Met-Thr-Trp-Asp-Pro-Ala-Gln-Pro-Pro-Arg (III), which sequence corresponds to amino acids 257–269 of cytochrome P450 IID6, a peptide fragment, characterized in that it consists of three amino acids whose sequence is of the following formula IV:

Thr-Trp-Asp (IV), which sequence corresponds to amino acids 261, 262 and 263 of human cytochrome P450 IID6, b—a second set of fragments, comprising at least one fragment of the sequence of cytochrome P450 IID6 between amino acid 282 and amino acid 351, and especially:

a peptide fragment characterized in that it consists of 70 amino acids, whose sequence is of the following formula V (SEQ ID NO:4):

Ala — Lys — Gly — Asn — Pro — Glu — Ser — Ser — Phe — Asn — Asp — (V)
Glu — Asn — Leu — Arg — Ile — Val — Val — Ala — Asp — Leu — Phe —
Ser — Ala — Gly — Met — Val — Thr — Thr — Ser — Thr — Thr — Leu —
Ala — Trp — Gly — Leu — Leu — Leu — Met — Ile — Leu — His — Pro —
Asp — Val — Gln — Arg — Arg — Val — Gln — Gln — Glu — Ile — Asp —
Val — Ile — Gly — Gln — Val — Arg — Arg — Pro — Glu — Met — Gly —
Asp — Gln — Ala, which sequence corresponds to amino acids 282–351 of human cytochrome P450 IID6;

a peptide fragment, characterized in that it consists of 13 amino acids, whose sequence is of the following formula VI (SEQ ID NO. 5):

Ala-Lys-Gly-Asn-Pro-Glu-Ser-Ser-Phe-Asn-Asp-Glu-Asn (VI), which sequence corresponds to amino acids 282–294 of cytochrome P450 1ID6, a peptide fragment, characterized in that it consists of 43 amino acids, whose sequence is of the following formula VII (SEQ ID NO.6):

Met — Val — Thr — Thr — Ser — Thr — Thr — Leu — Ala — Trp — Gly (VII)
Leu — Leu — Leu — Met — Ile — Leu — His — Pro — Asp — Val — Gln
Arg — Arg — Val — Gln — Gln — Glu-
— Ile — Asp — Asp — Val — Ile —
Gly — Gln — Val — Arg — Arg — Pro — Glu — Met — Gly — Asp, which sequence corresponds to amino acids 307–349 of cytochrome P450 IID6, a peptide fragment, characterized in that it consists of 31 amino acids, whose sequence is of the following formula Va (SEQ ID NO. 7):

Met — Ile — Leu — His — Pro — Asp — Val — Gln — Arg — Arg — Val (Va)
Gln — Gln — Glu — Ile — Asp — Asp — Val — Ile — G-
ly — Gln — Val —
Ile — Gly — Gln — Val — Arg — Arg — Pro — Glu — Met — Gly — Asp
Gln — Ala, which sequence corresponds to amino acids 321–351 of cytochrome P450 IID6, c—a third set of fragments, comprising at least one fragment of the sequence of cytochrome P450 IID6 between amino acid 349 and amino acid 389, and especially:

a peptide fragment, characterized in that it consists of 41 amino acids, whose sequence is of the following formula VIII (SEQ ID NO. 8):

Asp — Gln — Ala — His — Met — Pro — Tyr — Thr — Thr — Ala — Val (VIII)
Ile — His — Glu — Val — Gln — Arg — Phe — Gly — Asp — Ile — Val —
Pro — Leu — Gly — Met — Thr — His — Met — Thr — Ser — Arg —
Asp — Ile — Gly — Val — Gln — Gly — Phe — Arg — Ile, which sequence corresponds to amino acids 349–389 of human cytochrome P450 IID6, a peptide fragment, characterized in that it consists of 17 amino acids, whose sequence is of the following formula IX (SEQ ID NO. 9):

Gly-Met-Thr-His-Met-Thr-Ser-Arg-Asp-Ile-Gly-Val-Gln-Gly-Phe-Arg-Ile (IX), which sequence corresponds to amino acids 373–389 of human cytochrome P450 IID6, d—a fourth set of fragments, comprising at least one fragment of the sequence of cytochrome P450 IID6 between amino acid 410 and amino acid 429, and especially:

a peptide fragment, characterized in that it consists of 20 amino acids, whose sequence is of the following formula X(SEQ ID NO. 10):

Glu-Lys-Pro-Tyr-Pro-Glu-His-Phe-Leu-Asp-Ala-Gln-Gly-His-Phe-Val-Lys-Pro-Glu-Ala (X), which sequence corresponds to amino acids 410–429 of human cytochrome P450 IID6.

These peptides can in particular be prepared by synthesis, especially by the Merrifield method.

The subject of the present invention is also anti-human cytochrome P450 antibodies, characterized in that they consist of anti-peptide fragment antibodies as described in the invention.

According to an advantageous embodiment of the said antibodies, they consist of polyclonal antibodies.

These polyclonal antibodies are advantageously obtained by immunization of an appropriate mammalian, especially rabbit with a peptide conforming to the invention, optionally coupled to a suitable protein such as BSA (bovine serum albumin) or KLH (keyhole limpet haemocyanin).

According to another advantageous embodiment of the said antibodies, they consist of monoclonal antibodies specific for a human cytochrome P450 IID6-derived peptide fragment as defined above.

These anti-peptide fragment monoclonal antibodies are advantageously obtained, in a manner known per se, by fusion of splenic cells from mice immunized with an antigen consisting of a peptide fragment of cytochrome P450 IID6 as defined above, optionally coupled to a suitable protein such as BSA or KLH, with appropriate myelomatous cells.

The subject of the present invention is also an immunological reagent which can be used for the detection, diagnosis and monitoring of autoimmune hepatitis, characterized in that it is chosen from the group comprising the peptide fragments and anti-peptide antibodies conforming to the invention or a fragment thereof.

In particular, when the fragments of formulae II, III and IV, as defined above, are used as diagnostic reagents, they cause a positive response in all patients suffering from autoimmune hepatitis and the fragments of formulae Va, IX and X cause a positive response in most patients suffering from autoimmune hepatitis.

The subject of the present invention is also a process for the detection and/or diagnosis of autoimmune hepatitis, characterized in that it consists in detecting the autoantibodies which may be present in a biological fluid such as blood, by placing the said biological fluid in contact with at least one suitable immunological reagent conforming to the invention, to which the anti-LKM autoantibodies bind if such antibodies are present in the biological sample to be controlled, the reading of the result being revealed by an appropriate means, especially RIA, EIA or flow cytometry.

According to an advantageous embodiment of the said process, when the immunological reagent is a peptide fragment, the said biological fluid is brought into contact with a pool of peptides conforming to the invention.

According to an advantageous arrangement of this embodiment, the said pool comprises at least 4 different peptides.

According to an advantageous form of this arrangement, the first peptide comprises a peptide fragment chosen from the group consisting of the fragments of formulae I, II, III or IV; the second peptide comprises a peptide fragment of formula IX, the third peptide comprises a peptide fragment of formula X and the fourth peptide comprises a peptide fragment of formula Va.

The reagents and the process for detection conforming to the invention have the advantage of permitting a differential diagnosis between autoimmune hepatitis and the other hepatitides of viral origin.

The subject of the present invention is also agents for therapeutic and/or preventive use, characterized in that they consist of, or comprise as active constituent, a peptide conforming to the invention and/or its fragments, alone or conjugated or recombined or associated with other substances.

The subject of the present invention is also agents for therapeutic and/or preventive use, characterized in that they consist of, or comprise as active constituent, anti-peptide antibodies conforming to the invention, and/or their fragments, alone or conjugated or recombined or associated with other substances.

The subject of the present invention is in addition a
   diagnostic kit or box for the detection, diagnosis or monitoring of autoimmune hepatitis, characterized in that it comprises:

appropriate solid support suitably coated with at least one ligand chosen from the group comprising the peptides conforming to the invention, the antibodies conforming to the invention, the F(ab)'$_2$ fragments and the Fab' fragments of the said antibodies;

at least one bottle containing conjugates chosen from the group comprising the conjugates appropriate enzyme-appropriate human antibodies to Ig, the conjugates appropriate enzyme-antibodies to human Ig Fc fragment and the conjugates appropriate enzyme-anti-peptide antibodies conforming to the invention;

appropriate quantities or doses of an appropriate revealing substance.

In the case of a direct method, for example the anti-LKM antibodies of the patient become attached to the peptides conforming to the invention, previously attached to the solid support and conjugates of appropriate enzyme-appropriate human antibodies to Ig or conjugates of appropriate enzyme-antibodies to human Ig Fc fragment are introduced, bind with the patient's Ig and are then revealed in an appropriate manner.

In the case of an indirect method, for example conjugates of appropriate enzyme-anti-peptide antibodies conforming to the invention, enter into competition with the patient's antibodies in order to bind to the solid support coated with peptides or antibodies conforming to the invention.

In addition to the preceding arrangements, the invention further comprises other arrangements which will emerge from the description below which refers to exemplary embodiments of the process which is the subject of the present invention.

It should be understood, however, that these examples are given solely by way of illustration of the subject of the invention and do not constitute in any manner a limitation thereof.

EXAMPLE 1

Selection and preparation of the peptide fragments conforming to the invention.

a) Construction of the expression plasmids pEX627-LKMHC5 and pEX627-LKMC1.

LKMHC5 is a CDNA clone in the phage λGT-11 which encodes the human cytochrome P450 1ID6 (GUEGUEN M. et al., 1989, reference cited). The EcoRI-PstI fragment of cDNA (1007 bp) is subcloned into the plasmid EX-627, which permits the expression of a fusion protein (β-galactosidase/P450 IID6) in the bacterium *E. coli* pop 2136. The restriction map of cytochrome P450 IID6 is obtained from GenBank and used to create various constructs. The endonucleases used are: EcoRI, ApaI, BstEII, SauI Aval, StuI, PstI, EcoNI and PpuMI; the specific restriction sites are represented in FIG. 1. The procedures used for the restriction and ligation are those described in SAMBROOK et al., (Molecular cloning, Laboratory Manual, 1989, Cold Spring Harbor Laboratory). The various constructs obtained, designated by letters, correspond to various cytochrome P450 fragments as follows:

Construct A: amino acid sequence 125–152;
Construct B: sequence 125–239;
Construct C: sequence 125–273/428–458;
Construct D: sequence 428–458;
Construct E: sequence 125–273 (*);
Construct F: sequence 125–208/273–458;
Construct G: sequence 349–458;
Construct H: sequence 349–428 (▲);
Construct I: sequence 273–307 and
Construct J: sequence 349–389 (▲) (see FIG. 1).

Each of these constructs is cloned and analysed before expression in order to confirm that the predicted DNA size is indeed obtained.

In FIG. 1, the sign * indicates an antigenic site recognized by the sera of all the patients tested and the sign ▲ indicates other antigenic sites recognized by a certain number of patients.

The clone LKMC1 is a cDNA clone in the phage λGT-11 which encodes the rat cytochrome P450 db2. The EcoRI-BamHI fragment of LKMC1 (800 bp) is cloned into the plasmid pEX-627 and transfected into *E. coli* pop 2136. This makes it possible to test the peptide corresponding to the 5' region of the gene (encoding amino acid 1 to amino acid 125).

detection of the epitopes:

The complete protein P450 IID6 comprises 495 amino acids. The clone LKMHC5 EcoRI/PSTI, as defined above, which encodes amino acids 125 to 458, permits analysis of the C-terminal portion of the molecule, whereas the N-terminal region is analysed using a subclone EcoRI/BamHILKMC1, as defined above, and which encodes the amino acid sequence 1–266 of human cytochrome P450 IID6.

Figure 2:
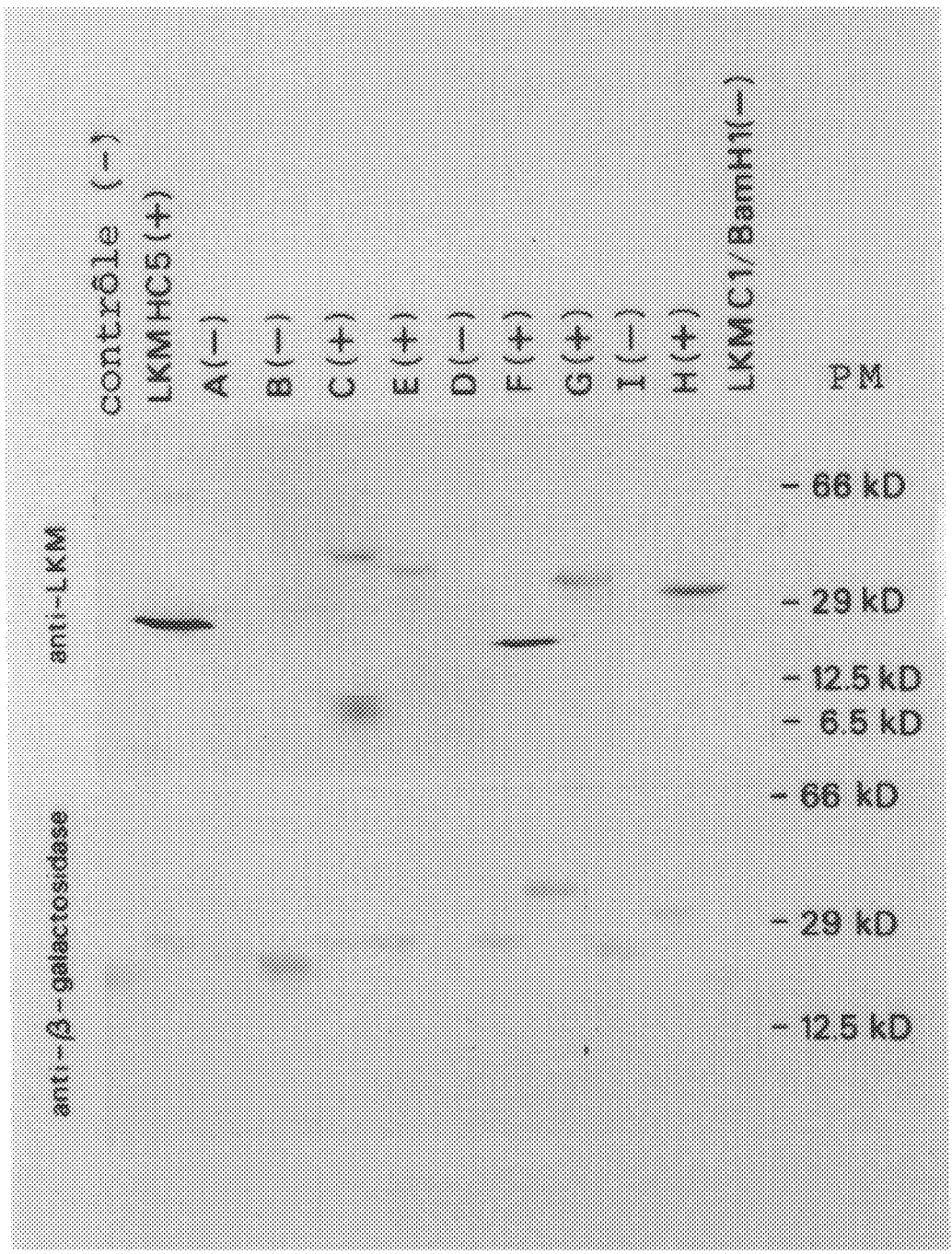
FIG. 2 is an immunoblot analysis of the fusion proteins P450 IID6/β-gal.

Analysis of these clones shows that a 70.4% homology exists between the $NH_2$-terminal portion of 125 amino acids of the rat protein P450-db2 (LKMC1) and the human protein P450 IID6. The DNA constructs as defined above, in the plasmid EX-627, made it possible to test various regions of the human protein P450 IID6, situated between amino acids 125 and 458. On the immunoblots, FIG. 2, all the LKM₇positive sera recognize the fusion proteins obtained from constructs C, E and F. Six out of the eleven sera tested recognize the constructs G, H and J. None of the sera of the patients tested recognizes the constructs A, B, D, I and LKMC1/BamHI. All the fusion proteins are recognized by anti-β-galactosidase antibodies. These results illustrate the presence of at least two antigenic sites on the human protein P450 IID6 recognized by the anti-LKM antibodies. The combined results for the constructs A(−), B(−), C(+), D(−) and E(+) show that a peptide region of 34 amino acids (amino acids 239 to 273 of the human protein P450 IID6) contains at least one of the epitopes recognized by all the LKM-positive sera tested. Since the constructs G, H and J are recognized by six of the eleven LKM-positive sera tested, another antigenic site is probably localized between amino acids 349 and 389. The region situated between constructs H and I was not tested specifically but was present in the construct F. A third epitope is situated between amino acids 307 and 349. The presence of multiple epitopes on an autoantigen is in favour of the hypothesis which considers that the autoimmune response is polyclonal. Similar results were obtained with other autoantigen-autoantibody systems and these were interpreted as the absence of a randomly produced mutation as the mechanism for the production of autoantibodies and make it possible to support the fact that the autoimmune response is induced by the antigen.

b) Expression and immunoblot analysis of the fusion proteins obtained from the various constructs of pEX-627-LKMHC5 and pEX-627-LKMC1/BamHI.

The expression of the fusion proteins from the cDNA constructs is described by STANLEY (Nucleic Acids Research, 1983, 11, 4077). 100 μl culture samples, for each fusion protein, are subjected to electrophoresis on an 8–20% SDS-polyacrylamide gel, transferred onto nitrocellulose and analysed by the immunoblot technique.

The first antibodies used for the immunoblot method are:

1) sera from patients responding positively to the anti-LKM antibodies;

2) sera from patients responding positively to the anti-SMA antibodies;

3) mouse anti-β-galactosidase antibodies; and 4) a normal human serum.

Depending on the origin of the first antibody, the second antibody is either a peroxydase-goat anti-human IgG conjugate, or a peroxydase-goat anti-mouse IgG conjugate (Biosys), at a dilution of 1/1000.

Rat liver and human liver microsomes and β-galactosidase, expressed by the plasmid pEX-627 not comprising the P450 DNA insert, are included on the same gels as positive controls and negative control respectively.

c) Synthesis of the peptides.

The solid-phase synthesis of the peptide is performed using an Applied Biosystems apparatus. The peptides are synthesized on a p-benzyloxybenzyl alcohol resin, using 9-fluoroenylmethoxycarbonyl (FMOC). The protected amino acid derivatives are obtained from Novabiochem and the other reagents from Applied Biosystems. The peptides are separated from the resin with a fluoroacetic acid:phenol:ethanedithiol:thio-anisole:water mixture (80:3:1:2:2) and purified by chromatography using a Nucleosil C8 300 A reversed-phase column. Three peptides are thus synthesized (sequences 241–260, 254–271 and 264–281) and have made it possible to analyse one of the regions (241–280) of the fusion protein, which is recognized by LKM-positive sera (see Table I below).

Peptide 241–260 is synthesized with an additional cystein residue at the $NH_2$-terminal end in order to avoid modification of the lysine 245 (Table I), during the coupling to bovine serum albumin.

TABLE I

| Cytochrome P450 IID6 peptides | ELISA test | Immunoblotting |
|---|---|---|
| Fragment 241–260 | − | − |
| Peptide of formula II (254–271) | + | + |
| Peptide of formula III (257–269) | + | + |
| Peptide of formula IX (373–389) | + | + |
| Peptide of formula X (410–429) | + | + |
| Peptide of formula Va (321–351) | + | + |
| Fragment 264–281 | − | − |
| Fragment 347–367 | − | − |
| Fragment 359–377 | − | − |
| Fragment 383–394 | − | − |
| Fragment 382–417 | − | − |

The major antigenic site localized between the amino acids 239 and 273 was also analysed using three synthetic peptides which cover the region between the amino acids 241 and 281 as seen in Table I above. One of the peptides covering the 254–271 region is recognized by all the LKM-positive sera when it is tested by ELISA and immunoblotting, whereas the other three peptides are not (Va, recognized by 8 patients/15; IX, recognized by 1 patient/15; X, recognized by 2 patients/15) * Insofar as the synthesized peptides II, III and Va overlap, the tripeptide Thr-Trp-Asp represents an essential portion of the epitope.

d) Coupling of the cytochrome P450 IID6-derived peptides with bovine serum albumin (BSA).

The different peptides and especially peptides 254–271 (peptide of formula II), 264–281 and 410–429 (peptide of formula X), are coupled to BSA via their free $NH_2$-terminal group, using glutaraldehyde (see especially E. HARLOW and D. LANE, 1988, Antibodies, A laboratory manual, Cold Spring Harbor Laboratory).

A number of peptides (241–260, 383–399, 392–417 and the peptide of formula X) carry an additional N-terminal cysteine residue which permits coupling to BSA via the sulphhydryl group of cysteine using an m-maleimidobenzoyl-N-hydroxysuccinimide ester.

EXAMPLE 2

ELISA test.

The peptides are redissolved in a PBS buffer, pH 7.4 and diluted in order to obtain concentrations of 0.1, 0.2, 0.5 and 1 µg/ml; 100 µl per well of each peptide solution are incubated overnight in microtitre plates containing 96 wells (IMMULON2a commercially available ELISAPLATE, Dynatech, Poly-Labo, Paris—FRANCE). The ELISA analysis is then performed as described in GUEGUEN M. et al., (Biochem. Biophys. Res. Commun., 1989, 159, 542), using the various human sera described above. The first antibodies are tested at dilutions ranging from $1/100$ to $1/12,800$. The alkaline phosphatase-conjugated goat anti-human IgG antibody is used as second antibody at a dilution of $1/1000$. The test is developed by adding 100 µl of p-nitrophenyl phosphate at a concentration of 1 mg/ml in a 0.05M $NaCO_3$ buffer, pH 9.8 and 0.001M $MgCl_2$. The results read after incubating for 30 minutes at room temperature are considered positive when they are higher by a factor of 2 compared with the control serum.

Figure 3:
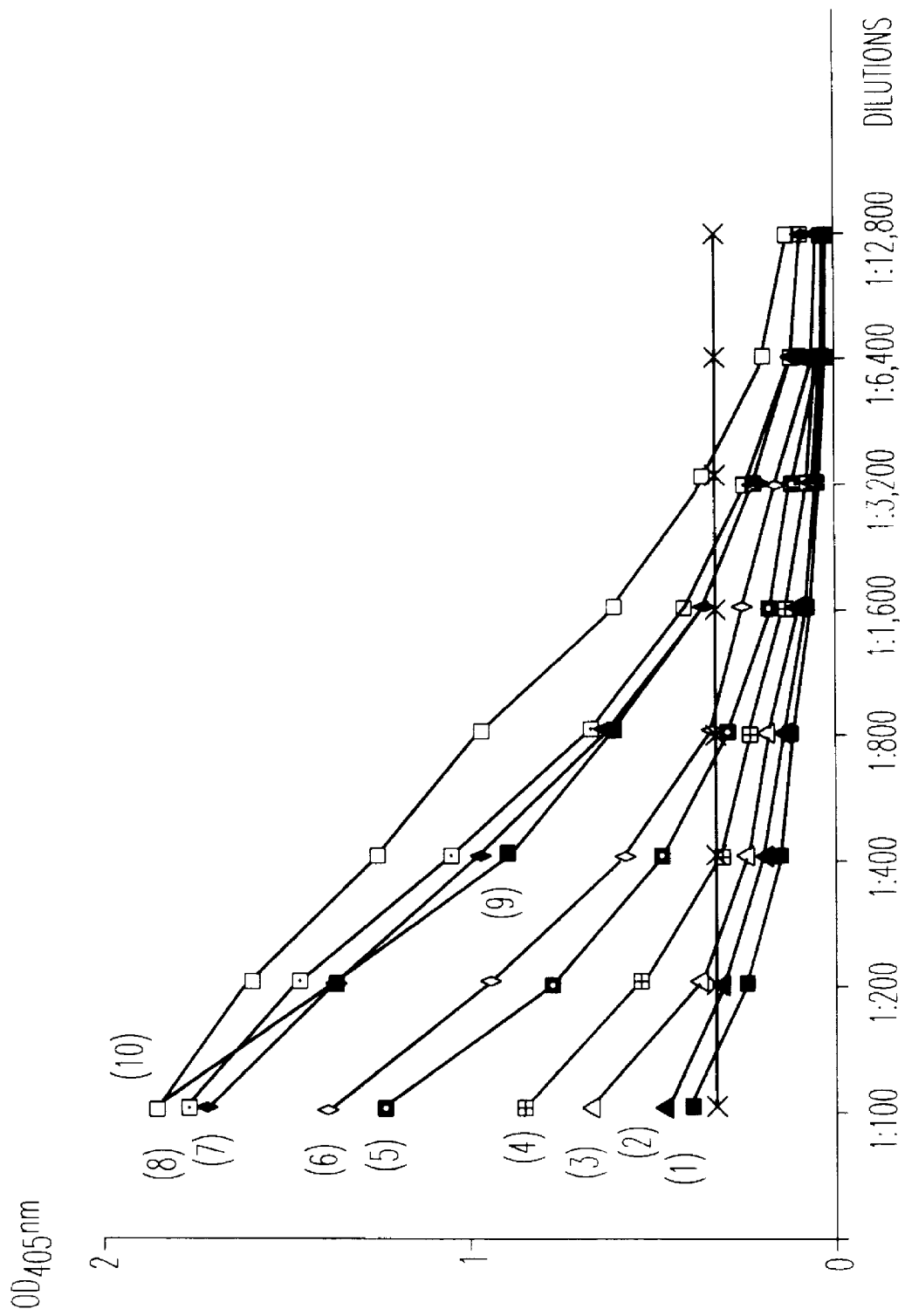
FIG. 3 is a graph depicting the results of an ELISA test performed on the sera of 10 patients.

FIG. 3 which comprises on the x-axis the dilutions and on the y-axis the optical densities, illustrates an ELISA test performed on the sera of 10 patients (curves 1 to 10), with, as antigen, a peptide comprising at least one fragment of the sequence 239–273 (peptides of formulae I, II, III or IV); the curve —x— corresponds to the upper limit of the normal.

As is evident from the above, the invention is not at all limited to its modes of implementations, embodiments and applications which have just been described more explicitly; on the contrary it encompasses all the variants which may occur to a specialist in this field without departing from the framework or the scope of the present invention.

I claim:

1. A reagent for the detection, diagnosis and monitoring of autoimmune hepatitis, consisting essentially of peptides consisting of SEQ ID NO:3, SEQ ID NO:7, SEQ ID NO:9 and SEQ ID NO:10.

2. A process for the detection and/or diagnosis of autoimmune hepatitis, comprising:
   (a) placing a biological fluid in which autoantibodies are to be detected in contact with
      (i) the reagent of claim 1; and
      (ii) an enzyme-labeled anti-human cytochrome P450 IID6 antibody which specifically binds to the reagent of claim 1;
   (b) detecting binding of the reagent of claim 1 to the enzyme-labeled anti-human cytochrome P450 IID6 antibody; and
   (c) correlating the binding detected in (b) to the presence of autoantibodies in the biological fluid.

3. A process for the detection and/or diagnosis of autoimmune hepatitis, comprising:
   (a) placing a biological fluid in which autoantibodies are to be detected in contact with the reagent of claim 1 to form a complex;
   (b) contacting the complex obtained in (a) with an enzyme-labeled anti-human Ig antibody;
   (c) detecting binding of the complex with the enzyme-labeled anti-human Ig antibody; and
   (d) correlating the binding detected in (c) to the presence of autoantibodies in the biological fluid.

4. A diagnostic kit for the detection, diagnosis or monitoring of autoimmune hepatitis which comprises:
   (a) a solid support coated with the reagent of claim 1;
   (b) anti-human cytochrome P450 IID6 antibodies which bind to the reagent of claim 1; and
   (c) enzyme-labeled anti-human IgG antibodies.

5. A diagnostic kit for the detection, diagnosis or monitoring of autoimmune hepatitis which comprises:
   (a) a solid support coated with the reagent of claim 1; and
   (b) enzyme-labeled anti-human IgG antibodies.

* * * * *